United States Patent [19]

Sauer et al.

[11] Patent Number: 5,616,131
[45] Date of Patent: Apr. 1, 1997

[54] APPARATUS AND METHOD FOR ANCHORING SURGICAL INSTRUMENTATION

[75] Inventors: Jude S. Sauer, Pittsford; Michael G. Oravecz, Rochester; Roger J. Greenwald, Holley, all of N.Y.

[73] Assignee: LaserSurge, Inc., Rochester, N.Y.

[21] Appl. No.: 425,035

[22] Filed: Apr. 18, 1995

Related U.S. Application Data

[63] Continuation of Ser. No. 950,429, Sep. 23, 1992, abandoned.

[51] Int. Cl.$^6$ ........................................ A61M 5/32
[52] U.S. Cl. .................... 604/174; 604/178; 604/179
[58] Field of Search ........................ 604/174, 175, 604/177, 178, 179, 180

[56] References Cited

U.S. PATENT DOCUMENTS

| | | |
|---|---|---|
| 1,380,447 | 6/1921 | Wescott . |
| 2,898,917 | 8/1959 | Wallace . |
| 3,176,690 | 4/1965 | H'Doubler ............................. 604/174 |
| 3,487,837 | 1/1970 | Petersen . |
| 3,789,852 | 2/1974 | Kim et al. . |
| 3,817,251 | 6/1974 | Hasson . |
| 4,392,854 | 7/1983 | Ibach . |
| 4,393,873 | 7/1983 | Nawash et al. .................... 604/174 X |
| 4,419,094 | 12/1983 | Patel . |
| 4,519,793 | 5/1985 | Galindo . |
| 4,579,120 | 4/1986 | MacGregor . |
| 4,583,977 | 4/1986 | Shishov et al. . |
| 4,593,681 | 6/1986 | Soni . |
| 4,617,933 | 10/1986 | Hasson . |
| 4,645,492 | 2/1987 | Weeks . |
| 4,650,473 | 3/1987 | Bartholomew et al. ................ 604/174 |
| 4,675,006 | 6/1987 | Hrushesky . |
| 4,683,895 | 8/1987 | Pohadorf ............................. 604/174 X |
| 4,869,719 | 9/1989 | Hogan ..................................... 604/174 |
| 4,906,233 | 3/1990 | Moriuchi et al. ....................... 604/174 |
| 4,915,694 | 4/1990 | Yamamoto et al. . |
| 4,936,826 | 6/1990 | Amarasinghe ..................... 604/175 X |
| 4,985,033 | 1/1991 | Boebel et al. . |
| 5,000,732 | 3/1991 | Banks et al. ........................ 604/175 X |
| 5,002,557 | 3/1991 | Hasson . |
| 5,073,169 | 12/1991 | Raiken . |
| 5,102,396 | 4/1992 | Bommarito . |
| 5,137,520 | 8/1992 | Maxson et al. . |

FOREIGN PATENT DOCUMENTS

| | | |
|---|---|---|
| 0232600 | 8/1987 | European Pat. Off. . |
| 949943 | 7/1947 | France . |
| 3713829 | 11/1988 | Germany . |

OTHER PUBLICATIONS

Open Laparoscopy: A Report of 150 Cases, The Journal of Reproductive Medicine, vol. 12, No. 6, Jun. 1974, pp. 234–238.

Karl Storz Endoskope brochure.

*Primary Examiner*—Nicholas D. Lucchesi

[57] ABSTRACT

An apparatus for anchoring surgical instrumentation to tissue having a collar with structure thereon for attaching the collar to a surgical instrument and suture receiving structure disposed peripherally on the collar, the suture receiving being configured and dimensioned to receive an anchoring suture therein. A method is disclosed for using the apparatus whereby at least one suture provided in the peripheral tissue adjacent the surgical instrumentation is wrapped within the receiving structure.

10 Claims, 4 Drawing Sheets

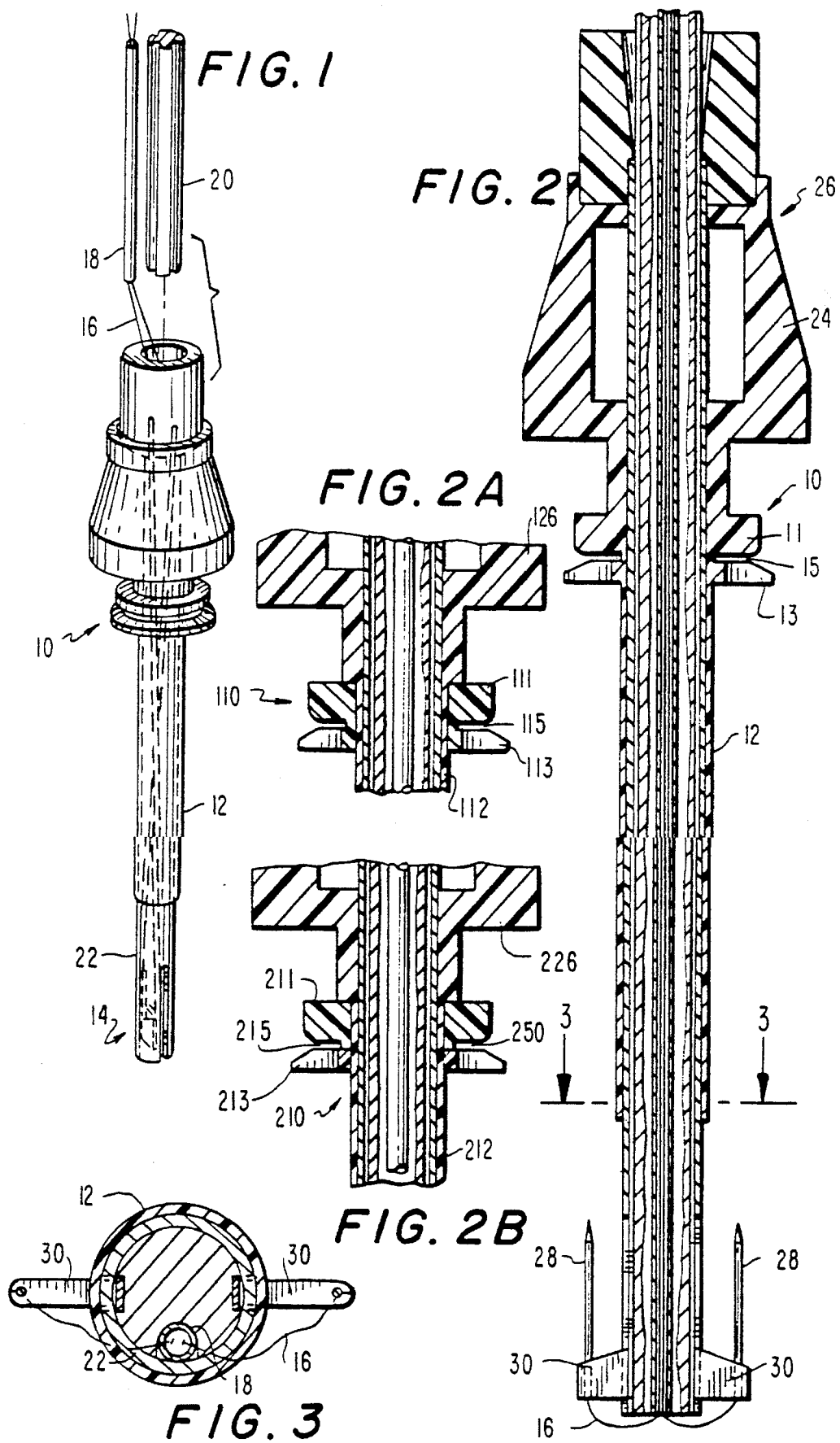

FIG. 8
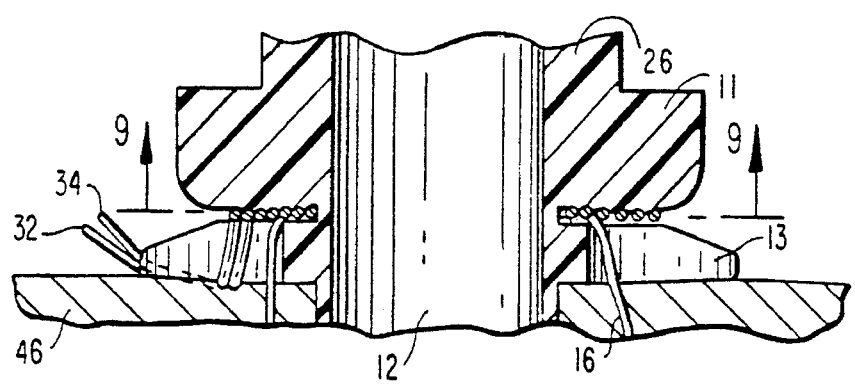
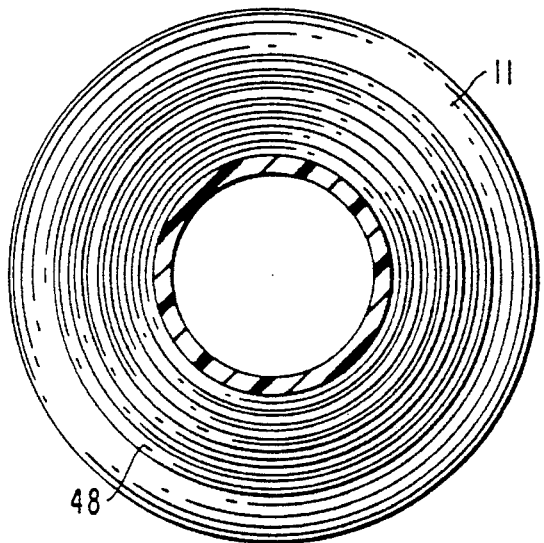
FIG. 9
FIG. 10
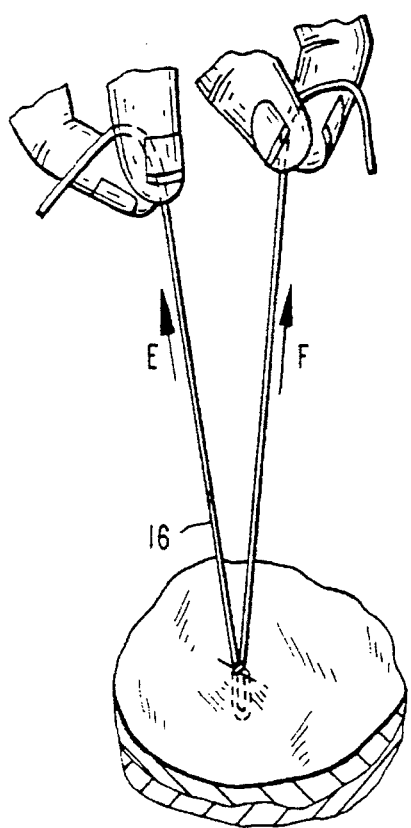

APPARATUS AND METHOD FOR ANCHORING SURGICAL INSTRUMENTATION

This is a continuation of application Ser. No. 07/950,429 filed on Sep. 23, 1992, now abandoned.

BACKGROUND OF THE INVENTION

1. Field of the Invention

This invention relates to apparatus for anchoring surgical instrumentation in place within a body opening and more particularly to apparatus for anchoring or stabilizing surgical instrumentation to a patient's body during endoscopic surgical procedures.

2. Description of the Related Art

In all types of surgical procedures, be they the open or closed type, it often becomes necessary to have certain instrumentation fixed with respect to either the patient or some other object within the surgical environment. This is desirable so that the surgeon or an assistant does not have to use their hands to hold the instrumentation in place, thereby limiting their capabilities during the procedure. In laparoscopic and endoscopic surgical procedures, holding instrumentation fixed relative to the patient or some other point is especially important. With laparoscopic and endoscopic surgery, a small incision or puncture is made in the patient's body to provide access for a tube or a cannula device. Once extended into the patient's body, the cannula allows for insertion or various surgical instruments such as scissors, dissectors, retractors, or biopsy instruments to perform diagnostics and/or surgery. Any sliding movement of the cannula into or out of the incision could cause internal damage to the patient or loss of the pneumoperitoneum, respectively.

Devices which anchor instruments during laparoscopic surgery are known. One such device is shown in U.S. Pat. No. 3,817,251 to Hasson which relates to a laparoscope cannula having a pair of hooks thereon for tying sutures in order to maintain the cannula in place with respect to the patient's abdomen. Also, U.S. Pat. No. 4,985,033 to Boebel et al., relates to a clamping device mounted on a surgical instrument for retaining the surgical instrument in a fixed position relative to the abdominal wall during surgery by securing fascial holding sutures therein.

Some disadvantages of devices such as these are that they require tying a knot in the suture or the use of moving parts to clamp the suture in place. Thus, in order to adjust the tension in the anchor suture, either the knot must be cut or the moving parts of the clamp must be manipulated to make the desired adjustment. In some cases the desired adjustment may require the application of a new suture to achieve the appropriate adjustment. In instances where the suture is made from the interior of the wound, much time must then be spent removing the instrumentation already in place and providing the appropriate suturing apparatus to form the suture. Accordingly, a continuing need exists for apparatus and methods which will provide quick, reliable anchoring of surgical instrumentation during surgical procedures and which will avoid the disadvantages of the prior art.

SUMMARY OF THE INVENTION

The present invention provides a novel instrument anchoring apparatus which includes a lightweight and easy to use device which may be operated quickly and efficiently. The device is easy to manufacture and is usable immediately with present instrumentation without requiring modification thereof.

The instrument anchoring apparatus of the present invention provides collar means, mounting means for attaching the collar means to at least a portion of a surgical instrument, and means peripherally disposed on the collar means for receiving a suture, the suture receiving means being configured and dimensioned to receive an anchoring suture therein. The anchoring apparatus may either be formed integrally with the instrument to be anchored, or it may be separate therefrom.

Preferably, at least one disk portion is provided having a peripheral groove formed thereon for receiving and retaining said suture. The disk may define at least one slot for receiving a suture, the slot being substantially transverse to a circumference of said disk. In another preferred embodiment a pair of disks are provided and may be formed integrally with each other or separable from each other. At least one of the disks may be provided with a plurality of annular grooves formed on a surface thereof such that a suture wrapped between the disks fits within the grooves as it is wrapped.

A method of anchoring surgical instrumentation to tissue is provided comprising the steps of: providing suture anchoring apparatus which comprises collar means, mounting means for attaching the collar means to at least a portion of a surgical instrument and means peripherally disposed on the collar means for receiving a suture, the suture receiving means being configured and dimensioned to receive an anchoring suture therein; providing at least one suture in the peripheral tissue adjacent surgical instrumentation; and wrapping the at least one suture within the receiving means.

BRIEF DESCRIPTION OF THE DRAWINGS

Preferred embodiments of the invention are described hereinbelow with reference to the drawings wherein:

FIG. 1 is a perspective exploded view with parts separated of the apparatus of the present invention as used in conjunction with other surgical instrumentation;

FIG. 2 is a side cross-sectional view of the apparatus of FIG. 1;

FIG. 2A is a partial, side cross-sectional view of an alternative embodiment of the apparatus of FIG. 1;

FIG. 2B is a partial, side cross-sectional view of another alternative embodiment of the apparatus of FIG. 1;

FIG. 3 is a cross-sectional view taken along line 3—3 of FIG. 2;

FIG. 8 is a cross-sectional view taken along line 8—8 of FIG. 7;

FIG. 9 is a cross-sectional view taken along line 9—9 of FIG. 8; and

FIG. 10 is a view of an incision wound being closed after usage of the apparatus of the present invention.

DETAILED DESCRIPTION OF THE PREFERRED EMBODIMENTS

Figure 5:
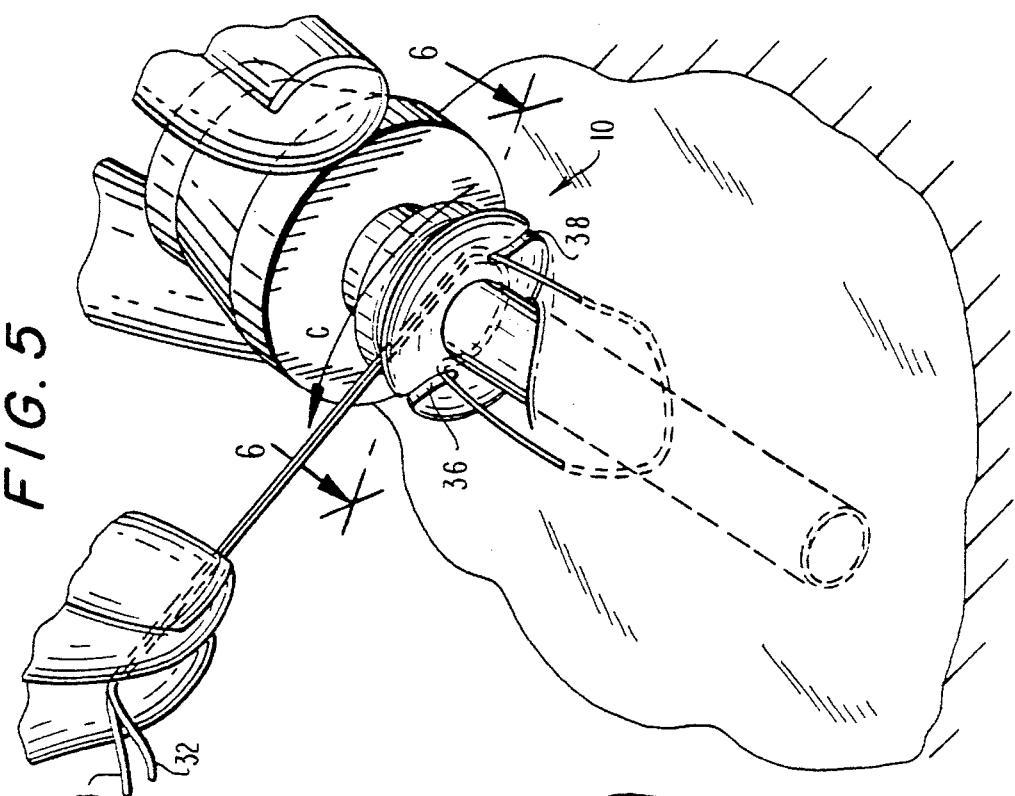
FIGS. 4 and 5 are perspective views of the operative use of the apparatus of FIG. 1.

Referring initially to FIG. 1, one embodiment of apparatus for anchoring surgical instrumentation in place in body openings is shown as cannula ring fastener device 10 particularly adapted for anchoring trocar cannulas to the peripheral tissue adjacent an endoscopic puncture wound. The following description will focus on specific apparatus and methods for anchoring trocar cannulas to the skin, fat and/or fascia surrounding the puncture wound by way of a suture placed from within the wound. It will be obvious to those having ordinary skill in the art that varying apparatus and methods may be devised which are within the spirit and scope of the invention described hereinbelow.

Except where noted otherwise, the materials utilized in the components of the apparatus generally include such materials as polycarbonate for housing sections and related components, and stainless steel, particularly for such components which transmit forces. One preferred material is a polycarbonate material available from General Electric Company under the trade name LEXAN. Other specific preferred materials such as nylon or glass filled nylon (for strength) may also be utilized. However, equivalent alternative materials will readily come to the mind of those skilled in the art.

FIG. 1 illustrates cannula ring fastener device 10 mounted near the proximal end of trocar cannula 12. Fastener device 10 is preferably in the form of a closed collar. Alternative configurations for fastener device 10, such as an open collar snap-fitted onto cannula 12 are also within the scope of the invention. Any suitable mounting methods may be used, such as, for example friction fitting device 10 around cannula 12. Trocar wound closure device 14 is shown mounted in cannula 12 for purposes of illustration only, to show one particular method of placing a suture which may be used with the invention. Trocar wound closure device 14 is the subject of co-pending U.S. application Ser. No. 07/876,511, filed Apr. 30, 1992 by Sauer et al., the contents of which are herein incorporated by reference.

Briefly, trocar wound closure device 14 places a suture in the peripheral tissue adjacent an endoscopic puncture wound by originating the suture from within the wound. The suture is placed by the use of a double armed suture, illustrated in FIGS. 2 and 3 as needles 28 and suture 16. Needles 28 are deployed by pushing down on plunger 20 (FIG. 1) which forces a pair of elongated flexible rods (not shown), attached to needle carders 30, toward the wall of tube 20. Needles 28, mounted on careers 30, are thereby deployed from tube 20 through slots formed therein. Closure device 14 is then pulled toward the entrance of the wound until needles 28 penetrate the fascia. Suture 16, which is held in suture carrier 18, feeds out of closure device 14 and follows a "U" shaped path through the tissue (see FIG. 4). Other conventional suturing methods may also be used in conjunction with the apparatus described herein to anchor various surgical instrumentation. For example, a suture may be lagged in the upper layers of tissue surrounding the instrumentation to be anchored and thereafter used with the apparatus of the invention as hereinafter described.

FIG. 2 illustrates a preferred embodiment of the invention wherein cannula ring fastener device 10 is formed integrally with handle 24 of trocar 26. Fastener device 10 includes upper disk portion 11 and lower disk portion 13 forming peripheral groove 15 therebetween for receiving and retaining suture 16. Trocar wound closure device 14 is shown having suture needles 28 deployed outwardly of tube 22 (also see FIG. 3) prior to retraction through the fascia (not shown) toward the exterior of the puncture wound.

Other preferred embodiments of the invention are illustrated in FIGS. 2A and 2B. In FIG. 2A, cannula ring fastener device 110 is shown as a unit separate from trocar 126 and is removably attached thereto. Fastener device 110 has upper disk portion 111, lower disk portion 113 and peripheral groove 115 disposed therebetween. Aside from being separable from trocar cannula 112, fastener device 110 functions and operates in substantially the same way as fastener device 10 described above.

In FIG. 2B, cannula ring fastener device 210 is shown as a two piece unit separate from trocar 226 and is removably attached thereto. Fastener device 210 differs from previously described embodiments in that upper disk 211 and lower disk 213 are separable from each other. Upper disk 211 is provided with spacer portions 250 to ensure precise relative positioning of upper disk 211 and lower disk 213. This feature allows for the distance between disks 211 and 213 to be smaller than required to slide suture 16 into groove 215. In this embodiment, disks 211 and 213 may initially be mounted on trocar cannula 212 at a distance somewhat greater than spacers 250 to allow for suture 16 to be wound into groove 215 as described above for previous embodiments. When it is desired to lock suture 16 between upper disk 211 and lower disk 213, the disks are pressed between the thumb and forefinger of each hand one on either side of fastener device 210 until lower disk 213 contacts spacer portions 250. To release suture 16 the disks are then separated by prying them apart and unwinding suture 16 therefrom.

Figure 4:
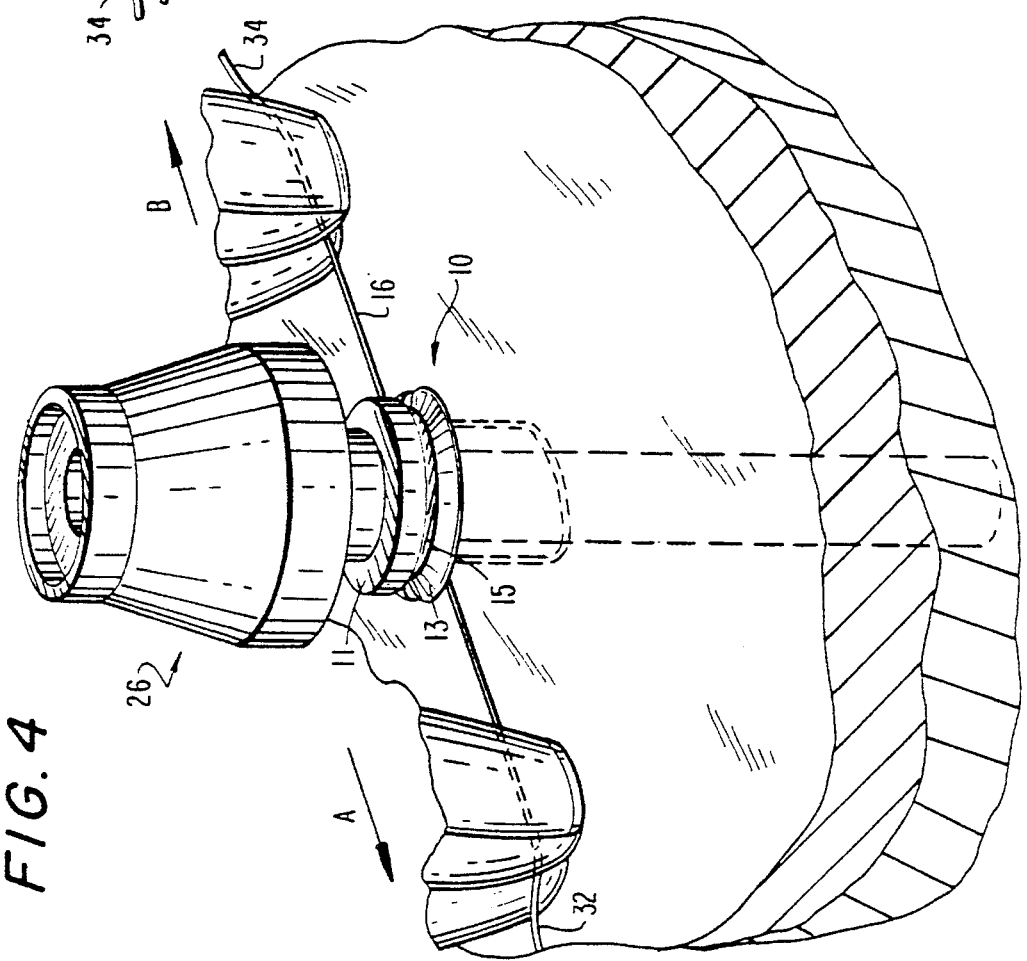
Figure 6:
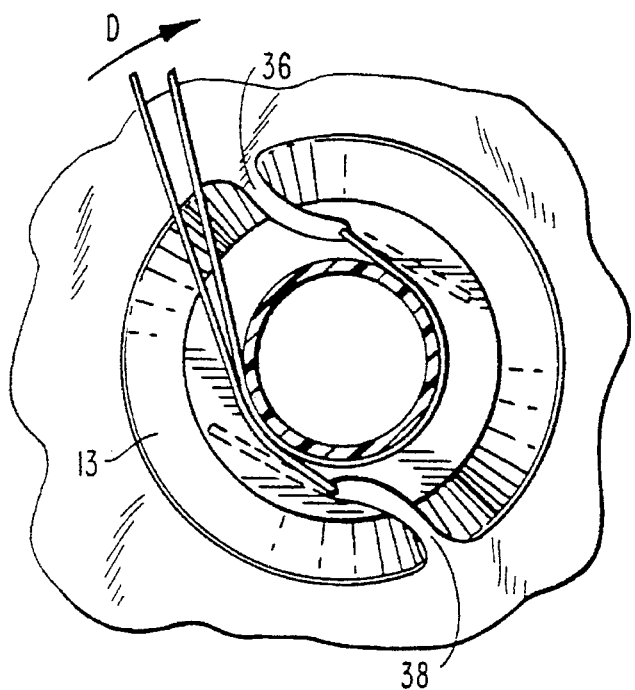
FIG. 6 is a cross-sectional view taken along line 6—6 of FIG. 5.
Figure 7:
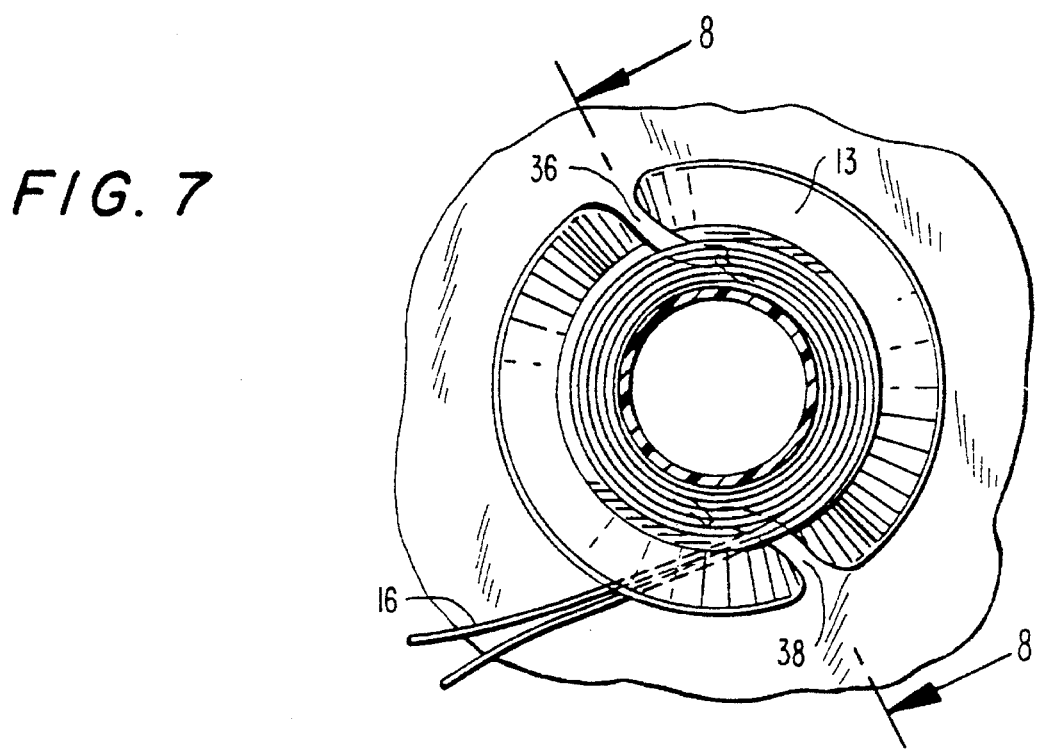
FIG. 7 is a top cut away view of the present invention.

The operation of cannula ring fastener device 10 will now be described with reference to FIGS. 4–8. Once suture needles 28 have been deployed from trocar wound closure device 14 and retracted through the several layers of fascia, closure device 14 is removed from trocar cannula 12. The surgeon then grasps needles 28 with appropriate instrumentation and removes needles 28 from needle carriers 30, pulling needles 28 until suture 16 is snug. Needles 28 are then cut away from suture 16 which is then grasped with either the surgeon's fingers or surgical instrumentation. Suture 16 is pulled substantially radially away from trocar 26 in the direction of arrows A and B, as illustrated in FIG. 4. At this time the surgeon may adjust the sutures by pulling on ends 32 and 34 so that the lengths of the exposed segments are of approximately equal length. Ends 32 and 34 are then laid out from their exit points radially about trocar cannula 12. End 32 of suture 16 is placed in suture slot 36 on cannula ring fastener device 10 and is pulled clockwise into peripheral suture retaining groove 15 disposed between upper disk portion 11 and lower disk portion 13. Suture end 32 is then pulled further in a clockwise direction until it reaches suture slot 38. Suture end 34 is then grasped and placed into suture slot 38 on cannula ring fastener device 10.

Next, end 34 is pulled until the portion of suture 16 adjacent slot 38 enters peripheral groove 15. Both ends 32 and 34 of suture 16 are then grasped together and pulled, wrapping both ends 32 and 34 clockwise, as illustrated by arrows C in FIG. 5 and D in FIG. 6, around groove 15 until approximately 1 to 2 inches of the shortest suture remain exposed. Ends 32 and 34 are then pulled back down through the nearest suture slot, either 36 or 38, such that ends 32 and 34 come out underneath lower disk portion 13 and are held in place between lower disk portion 13 and upper skin layer 46. Preferably, the opening formed by peripheral groove 15 is slightly more narrow than the diameter of suture 16, thereby causing an interference fit of the suture between the two disk portions. However, the opening of peripheral groove 15 may be the same as, or larger than the diameter of suture 16. Even with the opening being larger than the diameter of the suture material, the invention would still be effective in anchoring trocar cannula 12 as a result of wrapping suture 16 around peripheral groove 15 and tucking suture 16 beneath lower disk portion 13. Although the operation of cannula ring fastener device 10 has been described with a clockwise orientation of winding suture 16 within peripheral groove 15, one skilled in the art will readily appreciate that a counter clockwise winding may be used to achieve the same anchoring result of trocar 26.

FIG. 9 illustrates concentric annular grooves 48 provided along the surface of upper disk portion 11. These grooves help retain suture 16 within peripheral groove 15. Similar concentric annular grooves may also be provided on lower disk portion 13.

In FIG. 10, suture 16 is shown being pulled taut in the direction of arrows E and F with a surgical knot formed closing the surgical incision. Prior to forming the knot, suture 16 may be pulled to either side in order to expose fresh suture material to the wound site, and remove the length of suture material which was previously disposed at the site.

While the invention has been particularly shown and described with reference to the preferred embodiments, it will be understood by those skilled in the art that various modifications and changes in form and detail may be made therein without departing from the scope and spirit of the invention. Accordingly, modifications such as those suggested above but not limited thereto, are to be considered within the scope of the invention.

What is claimed is:

1. Apparatus for securing a surgical instrument disposed in tissue at an incision in a patient, comprising:
   a collar member having an outer wall;
   mounting means disposed on a portion of said collar member spaced from said outer wall for mounting said collar member to an outer surface of an instrument such that said mounting means is disposed around the instrument to permit selective longitudinal movement of the instrument relative to the apparatus; and
   a suture receiving portion formed on said outer wall of said collar ember for releasably receiving a suture secured in said tissue to anchor the instrument in said tissue wherein said suture receiving portion is defined by a pair of disks separated by a predetermined distance, said disks forming a peripheral groove therebetween for receiving and retaining said suture.

2. Apparatus according to claim 1 wherein at least one of said disks defines at least one slot for receiving a suture, said slot being substantially transverse to a circumference of said at least one disk.

3. Apparatus according to claim 1 wherein said disks are separable from each other.

4. Apparatus according to claim 1 wherein at least one of said disks has a plurality of annular grooves formed on a surface thereof such that said suture when wrapped between said disks fits within said grooves as it is wrapped.

5. Apparatus according to claim 1 wherein said collar member is adapted to be removably attached to said at least a portion of the surgical instrument.

6. A trocar cannula comprising:
   an elongated tubular member having a housing formed at a proximal end and a distal end adapted for insertion of said distal end into an incision in a patient's body, said tubular member having a longitudinal bore for accommodating a surgical instrument; and
   a collar member associated with said housing at said proximal end of said tubular member and disposed external to the patient's body, said collar member having outer wall, said outer wall having a peripheral groove disposed thereabout such that portions of said peripheral groove are disposed at least on opposite sides of said collar member for releasably receiving a suture secured in the patient's body for anchoring said tubular member in the incision in the patient's body wherein said retaining means includes a pair of disks separated by a predetermined distance said disks forming a peripheral groove therebetween for receiving and retaining said suture.

7. Apparatus according to claim 6 wherein at least one of said disks defines at least one slot for receiving said suture, said slot being substantially transverse to a circumference of said disk.

8. A trocar cannula according to claim 6 wherein said disks are separable from each other.

9. A trocar cannula according to claim 8 wherein at least one of said disks has a plurality of annular grooves formed on a surface thereof such that said suture is received within said grooves as it is wrapped between said disks.

10. Method of anchoring a surgical instrument to tissue comprising the steps of:
    (a) providing suture anchoring apparatus which comprises:
        i. collar means having an outer wall;
        ii. mounting means disposed on said collar means for attaching said collar means to at least a portion of a surgical instrument; and
        iii. means disposed on said outer wall of said collar means for receiving a suture, said suture receiving means being configured and dimensioned to receive said suture therein;
    (b) positioning said surgical instrument in an incision in tissue of a patient's body;
    (c) providing at least one suture in tissue adjacent said incision and said surgical instrument; and
    (d) wrapping said at least one suture about said collar means within said receiving means whereby said surgical instrument is held such that a longitudinal axis of said surgical instrument is positioned at a predetermined nonparallel angle relative to the surface of the tissue.

* * * * *